United States Patent
Fuentes Pananá et al.

(10) Patent No.: US 12,098,435 B2
(45) Date of Patent: Sep. 24, 2024

(54) METHOD FOR THE SIMULTANEOUS DETECTION AND QUANTIFICATION OF EPSTEIN-BARR VIRUS, CYTOMEGALOVIRUS, HUMAN HERPESVIRUS 6, HUMAN HERPESVIRUS 7 AND KAPOSI'S SARCOMA VIRUS USING A MULTIPLEX, REAL-TIME POLYMERASE CHAIN REACTION

(71) Applicant: HOSPITAL INFANTIL DE MÉXICO "FEDERICO GÓMEZ", Mexico City (MX)

(72) Inventors: Ezequiel M. Fuentes Pananá, Mexico City (MX); Abigail Morales Sánchez, Mexico City (MX); Yessica Sánchez Ponce, Mexico City (MX)

(73) Assignee: HOSPITAL INFANTIL DE MÉXICO "FEDERICO GÓMEZ", Mexico City (MX)

( * ) Notice: Subject to any disclaimer, the term of this patent is extended or adjusted under 35 U.S.C. 154(b) by 0 days.

(21) Appl. No.: 16/772,714

(22) PCT Filed: Feb. 14, 2019

(86) PCT No.: PCT/MX2019/000011
§ 371 (c)(1),
(2) Date: Jul. 28, 2020

(87) PCT Pub. No.: WO2019/117701
PCT Pub. Date: Jun. 20, 2019

(65) Prior Publication Data
US 2021/0032710 A1    Feb. 4, 2021

(30) Foreign Application Priority Data
Dec. 14, 2017   (MX) .................. MX/A/2017/016321

(51) Int. Cl.
*C12Q 1/68* (2018.01)
*C12Q 1/6844* (2018.01)
*C12Q 1/6851* (2018.01)
*C12Q 1/686* (2018.01)
*C12Q 1/70* (2006.01)

(52) U.S. Cl.
CPC ........... *C12Q 1/705* (2013.01); *C12Q 1/6844* (2013.01); *C12Q 1/6851* (2013.01); *C12Q 1/686* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2004/0038282 A1* | 2/2004 | Ladunga ................ | C07K 14/47 435/325 |
| 2011/0294147 A1* | 12/2011 | Burbelo ........... | G01N 33/56994 435/7.92 |
| 2012/0122700 A1* | 5/2012 | Medveczky ........... | C12Q 1/705 435/5 |
| 2012/0269854 A1* | 10/2012 | Chang .................... | A61P 31/22 424/229.1 |

FOREIGN PATENT DOCUMENTS

WO   WO-2004016219 A2 *  2/2004  ............ C12Q 1/705
WO   WO 2007/113388 A2   10/2007

OTHER PUBLICATIONS

Wernike et al. Development and validation of a triplex real-time PCR assay for the rapid detection and differentiation of wild type and glycoprotein E deleted vaccine strains of bovine herpesvirus type I. J Virological Methods. Vol. 174, p. 77-84, 2011.*
Sugita, S., et al. Use of multiplex PCR and real-time PCR to detect human herpes virus genome in ocular fluids of patients with uveitis. Br. J. Ophthalmol., vol. 92, p. 928-932, (2008).*
Lowe, T., et al. A computer program for selection of oligonucleotide primers for polymerase chai reactions. Nucleic Acids Research, vol. 18(7), p. 1757-1761, (1990).*
Sugita, S., et al. Virological analysis in patients with human herpes virus 6-associated occular inflammatory disorders. IOVS, vol. 53 (8), p. 4692-4698, (2012).*
Wada, K., et al. Simultaneous quantitation of Epstein-Barr virus, Cytomegalovirus, and human herpesvirus 6 DNA in samples from transplant recipients by multiplex real-time PCR assay. J Clin Microbiol., Vo. 45(5), p. 1426-1432, (2007).*
C. Costa, et al. "Herpesviruses Detection by Quantitative Real-Time Polymerase Chain Reaction in Bronchoalveolar Lavage and Transbronchial Biopsy in Lung Transplant: Viral Infections and Histopathological Correlation", Elsevier, Transplantation Proceedings, 42, (2010), pp. 1270-1274.
Masahiro Fujimuro, et al. "Multiplex PCR-based DNA array for simultaneous detection of three human herpesviruses, EVB, CMV and KSHV", Science Direct, Experimental and Molecular Pathology 80 (2006) pp. 124-131.
Hiroshi Kimura, et al. "Quantitative Analysis of Epstein-Barr Virus Load by Using a Real-Time PCR Assay", Journal of Clinical Microbiology, Jan. 1999, vol. 37, No. 1, pp. 132-136.
Y. Ono, et al. "Simultaneous Monitoring by Real-Time Polymerase Chain Reaction of Epstein-Barr Virus, Human Cytomegalovirus, and Human Herpesvirus-6 in Juvenile and Adult Liver Transplant Recipients", Elsevier, Complications, pp. 3578-3582.

(Continued)

*Primary Examiner* — Suryaprabha Chunduru
(74) *Attorney, Agent, or Firm* — MORGAN, LEWIS & BOCKIUS LLP

(57) ABSTRACT

The present invention relates to a method for the multiple and simultaneous detection and quantification of any combination of beta and gamma genera human herpesviruses: Epstein-Barr virus (EBV), Cytomegalovirus (CMV), Human herpesvirus type 6 (HHV6), Human Herpesvirus type 7 (HHV7) and Kaposi's Sarcoma Virus (KSV) and the beta-actin human endogenous gene by DNA amplification reaction using the multiplex polymerase chain reaction in real time.

3 Claims, 6 Drawing Sheets

Specification includes a Sequence Listing.

(56) References Cited

OTHER PUBLICATIONS

Yessica Sánchez-Ponce, et al. "Simultaneous Detection of Beta and Gamma Human Herpesviruses by Multiplex qPCR Reveals Simple Infection and Coinfection Episodes Increasing Risk for Graft Rejection in Solid Organ Transplantation", Viruses 2018, 10, 730; doi: 10.3390/v10120730, 19 pages.

Kaoru Wada, et al. "Simultaneous Quantification of Epstein-Barr Virus, Cytomegalovirus, and Human Herpesvirus 6 DNA in Samples from Transplant Recipients by Multiplex Real-Time PCR Assay", Journal of Clinical Microbiology, vol. 45, No. 5, May 2007, pp. 1426-1432.

* cited by examiner

SEQUENCE LISTING

```
<160> NUMBER OF SEQ ID NOS: 18

<210> SEQ ID NO 1
<211> LENGTH: 21
<212> TYPE: DNA
<213> ORGANISM: Artificial Sequence
<220> FEATURE:
<223> OTHER INFORMATION: Forward primer ID VEB_F

<400> SEQUENCE: 1
ccctgtttat ccgatggaat g                                              21

<210> SEQ ID NO 2
<211> LENGTH: 19
<212> TYPE: DNA
<213> ORGANISM: Artificial Sequence
<220> FEATURE:
<223> OTHER INFORMATION: Reverse primer ID VEB_R

<400> SEQUENCE: 2
cggaagccct ctggacttc                                                 19

<210> SEQ ID NO 3
<211> LENGTH: 23
<212> TYPE: DNA
<213> ORGANISM: Artificial Sequence
<220> FEATURE:
<223> OTHER INFORMATION: Probe sequence
<220> FEATURE:
<221> NAME/KEY: misc_feature
<222> LOCATION: (1)..(1)
<223> OTHER INFORMATION: FAM bound fluorophore
<220> FEATURE:
<221> NAME/KEY: misc_feature
<222> LOCATION: (23)..(23)
<223> OTHER INFORMATION: BHQ1a bound quencher

<400> SEQUENCE: 3
tgtacacgca cgagaaatgc gcc                                            23

<210> SEQ ID NO 4
<211> LENGTH: 25
<212> TYPE: DNA
<213> ORGANISM: Artificial Sequence
<220> FEATURE:
<223> OTHER INFORMATION: Forward primer ID CMV_F

<400> SEQUENCE: 4 gctacaaatag cctcttcctc atctg                                         25

<210> SEQ ID NO 5
<211> LENGTH: 22
<212> TYPE: PRT
<213> ORGANISM: Artificial Sequence
<220> FEATURE:
```

```
<223> OTHER INFORMATION: Reverse primer ID CMV_R

<400> SEQUENCE: 5

Gly Ala Cys Thr Ala Gly Thr Gly Thr Gly Ala Thr Gly Cys Thr Gly
1               5                   10                  15

Gly Cys Cys Ala Ala Gly
            20

<210> SEQ ID NO 6
<211> LENGTH: 30
<212> TYPE: PRT
<213> ORGANISM: Artificial Sequence
<220> FEATURE:
<223> OTHER INFORMATION: Probe sequence
<220> FEATURE:
<221> NAME/KEY: MISC_FEATURE
<222> LOCATION: (1)..(1)
<223> OTHER INFORMATION: JOE bound fluorophore
<220> FEATURE:
<221> NAME/KEY: MISC_FEATURE
<222> LOCATION: (27)..(27)
<223> OTHER INFORMATION: BHQ1a bound quencher

<400> SEQUENCE: 6

Ala Gly Cys Cys Thr Gly Ala Gly Gly Thr Thr Ala Thr Cys Ala Gly
1               5                   10                  15

Thr Gly Thr Ala Ala Thr Gly Ala Ala Gly Cys Gly Cys Cys
            20                  25                  30

<210> SEQ ID NO 7
<211> LENGTH: 21
<212> TYPE: DNA
<213> ORGANISM: Artificial Sequence
<220> FEATURE:
<223> OTHER INFORMATION: Forward primer ID ACT_F

<400> SEQUENCE: 7
ccaggctaac ctcggaaatc t                                        21

<210> SEQ ID NO 8
<211> LENGTH: 21
<212> TYPE: DNA
<213> ORGANISM: Artificial Sequence
<220> FEATURE:
<223> OTHER INFORMATION: Reverse primer ID ACT_R

<400> SEQUENCE: 8
catcgtcatt cctgtgcaac t                                        21

<210> SEQ ID NO 9
<211> LENGTH: 20
<212> TYPE: DNA
<213> ORGANISM: Artificial Sequence
<220> FEATURE:
<223> OTHER INFORMATION: Probe sequence
<220> FEATURE:
<221> NAME/KEY: misc_feature
<222> LOCATION: (1)..(1)
<223> OTHER INFORMATION: Cy5 bound fluorophore
<220> FEATURE:
<221> NAME/KEY: misc_feature
<222> LOCATION: (20)..(20)
<223> OTHER INFORMATION: BHQ3a bound quencher

<400> SEQUENCE: 9
tggggtgccg gctctctgct                                          20
```

```
<210> SEQ ID NO 10
<211> LENGTH: 22
<212> TYPE: DNA
<213> ORGANISM: Artificial Sequence
<220> FEATURE:
<223> OTHER INFORMATION: Forward primer ID HVH6_F

<400> SEQUENCE: 10
cgactctcac cctactgaac ga                                            22

<210> SEQ ID NO 11
<211> LENGTH: 21
<212> TYPE: DNA
<213> ORGANISM: Artificial Sequence
<220> FEATURE:
<223> OTHER INFORMATION: Reverse primer ID HVH6_R

<400> SEQUENCE: 11
gaggctggcg tcgtagtaga a                                             21

<210> SEQ ID NO 12
<211> LENGTH: 28
<212> TYPE: DNA
<213> ORGANISM: Artificial Sequence
<220> FEATURE:
<223> OTHER INFORMATION: Probe sequence
<220> FEATURE:
<221> NAME/KEY: misc_feature
<222> LOCATION: (1)..(1)
<223> OTHER INFORMATION: FAM bound fluorophore
<220> FEATURE:
<221> NAME/KEY: misc_feature
<222> LOCATION: (28)..(28)
<223> OTHER INFORMATION: BHQ1a bound quencher

<400> SEQUENCE: 12
agccacagca gccatctaca tctgtcaa                                      28

<210> SEQ ID NO 13
<211> LENGTH: 24
<212> TYPE: DNA
<213> ORGANISM: Artificial Sequence
<220> FEATURE:
<223> OTHER INFORMATION: Forward primer ID HVH7_F

<400> SEQUENCE: 13
cggaagtcac tggagtaatg acaa                                          24

<210> SEQ ID NO 14
<211> LENGTH: 25
<212> TYPE: DNA
<213> ORGANISM: Artificial Sequence
<220> FEATURE:
<223> OTHER INFORMATION: Reverse primer HVH7_R

<400> SEQUENCE: 14
atgctttaaa catcctttct ttcgg                                         25

<210> SEQ ID NO 15
<211> LENGTH: 24
<212> TYPE: DNA
<213> ORGANISM: Artificial Sequence
<220> FEATURE:
<223> OTHER INFORMATION: Secuencia sonda
<220> FEATURE:
<221> NAME/KEY: misc_feature
<222> LOCATION: (1)..(1)
<223> OTHER INFORMATION: JOE bound fluorophore
<220> FEATURE:
```

```
<221> NAME/KEY: misc_feature
<222> LOCATION: (24)..(24)
<223> OTHER INFORMATION: BHQ1a bound quencher

<400> SEQUENCE: 15
ctcgcagatt gcttgttggc catg                                          24

<210> SEQ ID NO 16
<211> LENGTH: 20
<212> TYPE: DNA
<213> ORGANISM: Artificial Sequence
<220> FEATURE:
<223> OTHER INFORMATION: Forward primer ID VSK_F

<400> SEQUENCE: 16
agttatgggc gactggtctg                                               20

<210> SEQ ID NO 17
<211> LENGTH: 20
<212> TYPE: DNA
<213> ORGANISM: Artificial Sequence
<220> FEATURE:
<223> OTHER INFORMATION: Reverse primer ID VSK_R

<400> SEQUENCE: 17
ggatggaaga cgagatccaa                                               20

<210> SEQ ID NO 18
<211> LENGTH: 20
<212> TYPE: DNA
<213> ORGANISM: Artificial Sequence
<220> FEATURE:
<223> OTHER INFORMATION: Probe sequence
<220> FEATURE:
<221> NAME/KEY: misc_feature
<222> LOCATION: (1)..(1)
<223> OTHER INFORMATION: Cy5 bound fluorophore
<220> FEATURE:
<221> NAME/KEY: misc_feature
<222> LOCATION: (20)..(20)
<223> OTHER INFORMATION: BHQ3a bound quencher

<400> SEQUENCE: 18
aagtccgtat gggtcattgc                                               20
```

METHOD FOR THE SIMULTANEOUS DETECTION AND QUANTIFICATION OF EPSTEIN-BARR VIRUS, CYTOMEGALOVIRUS, HUMAN HERPESVIRUS 6, HUMAN HERPESVIRUS 7 AND KAPOSI'S SARCOMA VIRUS USING A MULTIPLEX, REAL-TIME POLYMERASE CHAIN REACTION

CROSS-REFERENCE TO RELATED APPLICATIONS

This application is a U.S. national phase application of a PCT Application No. PCT/MX2019/000011 filed on Feb. 14, 2019, which claims priority to a Mexican Patent Application No. MX/a/2017/016321 filed in Mexico on Dec. 14, 2017, the disclosure of which is incorporated herein by reference in its entirety.

FIELD OF THE INVENTION

Transplantation is one of the most important medical advances and currently continues to represent the only curative possibility for patients with terminal organ failure in whom there is no possibility of remission with conventional therapy. Viral infections represent one of the main risks that a transplant patient can face. The most frequent are given by the group of herpesviruses which can act in concert, enhancing their pathogenic effects. Therefore, it is extremely important to have a method for the detection and quantification of DNA of any human herpesvirus and a combination thereof.

SEQUENCE LISTING

The instant application contains a Sequence Listing which has been submitted electronically in ASCII format and is hereby incorporated by reference in its entirety. Said ASCII copy, created on Jun. 30, 2022, is named 116384-5005-US_ST25.txt and is 8,192 bytes in size.

BACKGROUND OF THE INVENTION

The Global Organization for Observation on Donation and Transplantation, associated with the World Health Organization, estimates that in 2014 119,873 solid organ transplants were performed, mainly kidney, liver and heart, these data include both children and adults (1).

There is a high risk that a transplant patient will face various complications during the post-transplant period, such as graft rejection or graft-versus-host disease. To reduce this risk, immunosuppression therapies are used, however, these therapies increase the risk of the appearance of infections. Viral infections, by themselves or as risk factors for lymphoproliferative diseases, constitute one of the main causes of morbidity and mortality in transplant patients (2).

The most frequent viral infections in solid organ transplant patients are those caused by the herpesvirus group, this group presents a wide cellular tropism, mainly infecting cells of the immune system. Herpesviruses are divided into three subfamilies: Alphaherpesvirinae, Betaherpesvirinae Gammaherpesvirinae (3).

Because herpesviruses are ubiquitous and the vast majority of the population is positive for them, simple positivity does not represent a finding of clinical importance. However, in specific situations, for example, in individuals with primary immunodeficiencies, acquired or associated with pharmacological treatments, a high load of herpesviruses may represent a high risk for said individual.

Currently, there is no global consensus about which viral loads should be considered of clinical relevance, even for EBV and CMV, which are the viruses that are most frequently monitored in immunocompromised patients. The literature is very heterogeneous in the following aspects (4-9).

a) The type of sample. There are reports of measurement of viral loads in plasma, serum, mononuclear cells or peripheral blood leukocytes, and others prefer to use whole blood.

b) Viral load report. Reports can be given in viral copies per µg of DNA, per ml of whole blood or serum/plasma or per number of cells.

c) Proposed clinical thresholds. For EBV and CMV, which are the most studied viruses, there are authors who consider relevant viral loads ranging from 200 copies/µg of DNA to those authors who only take into account samples that exceed 1400 copies/µg of DNA, with other reports indicating intermediate values.

Human beta and gamma herpesviruses comprise 5 agents that are acquired from the first years of life and infect the majority of the world population. Beta human herpesviruses are: Cytomegalovirus (CMV), Human herpesvirus type 6 (HHV6), Human herpesvirus type 7 (HHV7). Human gamma herpesviruses are: Epstein-Barr virus (EBV) and Kaposi's Sarcoma virus (KSV).

They are enveloped viruses whose genome is made up of double-stranded DNA. After infecting the host cell, they remain in the nucleus as episomes (circular genome). They are characterized by showing a biphasic replication cycle consisting of a latent phase and a lytic phase. In the latent phase, there is little or no expression of viral genes, while in the lytic phase, high gene expression and production of viral particles occur (3). However, both phases of the viral cycle are associated with the development of diseases ranging from mild or self-limited to severe and fatal, such as pneumonitis, hepatitis, encephalitis, spinal cord suppression, lymphoproliferative diseases, etc. Additionally, the EBV and KSV gammaherpesviruses are oncogenic agents associated with the development of various types of cancer, including aggressive lymphomas, carcinomas, and sarcomas (10).

Immunodeficient individuals such as neonates, with human deficiency virus (HIV) infection, with suppression of the immune system due to chemotherapeutic treatment, with solid organ post-transplantation pharmacological immunosuppression or hematopoietic progenitor cells are especially vulnerable to diseases caused by one or more of beta and gamma herpesviruses.

Since all beta and gamma herpesviruses infect cells of the immune system, they can indirectly produce immune compromise, which favors co-infection events by opportunistic agents including the herpesviruses themselves. This and other viral cooperation mechanisms contribute to the presentation of multiple infections that are of higher risk for patients (11).

The detection of viral loads of beta and gamma herpesviruses is of vital importance in the timely diagnosis of diseases caused by said agents, especially in immunosuppressed individuals, who can suffer simultaneous and recurrent infections. Quantification of viral loads guides antiviral treatment and, in case of transplant patients, is essential for the administration of adequate doses of immunosuppressive drugs.

In this context, several strategies have been previously developed to monitor beta and gamma herpesvirus infections using different methodologies. Currently, the PCR (polymerase chain reaction) technique is considered the most sensitive and fastest technique in detecting nucleic acids of pathogens from practically any type of biological sample. The technique was invented by Kary B. Mullis and is described in U.S. Pat. Nos. 4,683,195, 4,683,202, 4,800, 159, 4,889,818, 4,965,188, 5,008,182, 5,038,852, 5,079,352, 5,176,995, 5,310,652, 5,310,893, 5,322,770, 5,333,675, 5,352,600, 5,774,553, among others.

The development of the PCR technique has been expanding and diversifying in different methodologies including multiplex PCR. This consists of the simultaneous detection of different targets from the use of several pairs of primers in the same reaction. The initiators must be designed in such a way that they all work at the same alignment temperatures and under the same reaction conditions. Specifically, for real-time PCR, oligonucleotides labeled with different fluorophores are also used, which make it possible to distinguish the different products of the reaction. In the diagnosis of diseases caused by pathogens, multiplex PCR has been extremely useful because the obtaining of results occurs significantly faster and with less cost and laboratory work since the detection of various agents is carried out in the same reaction (12).

Pozo et al., developed a method for the simultaneous detection of EBV beta and gamma herpesviruses, CMV, HHV6, HHV7 and KSV, using nested endpoint PCR (13). Detection is directed at a highly conserved region of the DNA polymerase gene of the different herpesviruses. According to the results shown by the authors, the technique is specific, excluding the possibility of obtaining false positives even in the presence of agents as close as human herpesviruses (HHV) 1, 2 and 3. However, a disadvantage of this methodology is as it is a nested endpoint PCR technique, it requires two successive rounds of amplification and the performance of an additional electrophoresis assay to observe the amplification of the product of interest, which increases the laboratory work, the cost of the test and the detection time.

The technique has an estimated sensitivity between 10 and 100 copies depending on the monitored herpesvirus. However, since it is not a quantitative technique, it is only possible to know if the agent is present or not in the tested sample, without being able to know the number of viral copies present. The quantitative detection of agents such as EBV and CMV and KSV in conditions of post-transplant immunosuppression and/or due to HIV infection has been essential in the prevention of graft rejection, cytomegalovirus disease, post-transplant lymphoproliferative disease and presentation of post-transplant lymphomas and sarcomas since it has allowed immunosuppressive and antiviral drugs to be dosed more effectively (14). According to the above, quantitative real-time PCR techniques in multiplex format are currently the best option for monitoring beta and gamma herpesviruses.

Wada et al. developed a real-time PCR assay to simultaneously quantify EBV, CMV, and HHV6 herpesviruses (15). They used fluorescent probes labeled with 3 different fluorophores to detect the three herpesviruses under study. The specificity of the reaction was determined using DNA from different standard strains of HHV 1, 2, 3, EBV, CMV, HHV7 as well as a clinical isolate of HHV6. Viral load determination was made from a standard curve of plasmids containing virus genomic fragments. The minimum detection level was 2 copies for each virus with 95% confidence. Detection in triplex format proved to have practically the same sensitivity as the simple format. This was corroborated in a set of whole blood and plasma samples from transplant patients obtaining a high correlation in the viral load results in both formats, finding only some discordant measurements in samples with low loads that were around the detection limit.

The methodology developed by Wada et al., is useful in monitoring transplant patients who require continuous monitoring of viral loads of these agents. In this technique, however, other herpesviruses that are of equal importance in the management of immunocompromised patients are left out. Such agents are HHV7 and KSV. HHV7 is commonly reactivated in transplanted individuals where it can cause fever, spinal cord suppression, encephalitis, pneumonia, among other conditions (16, 17). KSV is an oncogenic virus strongly associated with the development of lymphomas and sarcomas in pharmacologically immunosuppressed individuals or by HIV infection (18, 19). On the other hand, this methodology, in which the presence of viral genomes in blood cells is determined, requires an additional test evaluating the quality of the sample in terms of DNA integrity and the presence of PCR inhibitors, which requires more time and cost of realization as well as more biological sample.

Of the methods described above, in some cases it will be necessary to carry out at least 3 and up to 7 PCR assays to determine if the test sample contains complete DNA and free of reaction inhibitors, and then if any combination of the EBV, CMV, HHV6, HHV7, KSV virus is present. In other cases, after three reactions, even when the sensitivity of the test is very high (nested PCR), the number of viral copies present in the biological samples will not be known; eventually, it will be necessary to perform a quantitative method to determine the viral load and thus estimate the doses of antiviral and immunosuppressive drugs required by patients infected with these agents and at risk of developing associated pathologies or morbidities already present at the time of detection.

In view of the foregoing and with the purpose of solving the limitations found, the method proposed here has the objective of improving all those previously described in various aspects. In terms of time for carrying out the test, it is significantly less, since the results of both DNA sample quality and viral load are obtained in a single run. For this same reason, the test requires a smaller amount of biological sample and is also less costly since it requires fewer reagents. The method is more sensitive in the sense that several herpesviruses infection is ruled out in a single run. A test of these characteristics is therefore essential in the diagnosis of patients at risk of developing diseases due to the aforementioned herpesviruses or in the treatment of patients who already have said diseases.

DETAILED DESCRIPTION OF THE INVENTION

Figure 1:
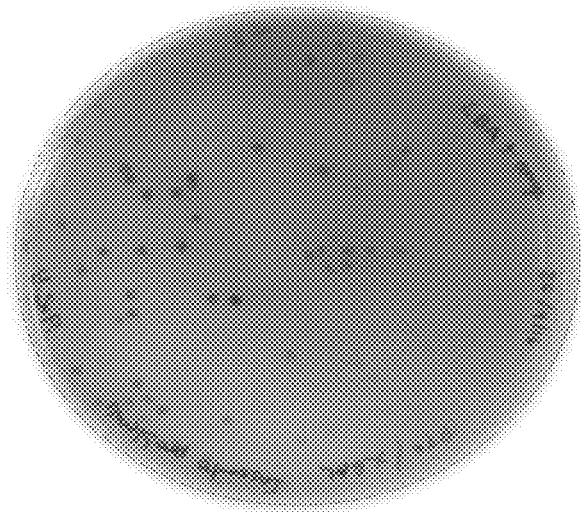
FIG. 1. Bacteria successfully transformed into white indicated with red arrows. In this example, *E. coli* bacteria of the DH5α strain were transformed with the commercial vector pGEM-T Easy (Promega) bound to the HHV6 gene fragment.

The present invention describes and claims a method for the detection of the human endogenous beta-actin gene and for the detection and quantification of DNA of any combination of human herpesviruses: Epstein-Barr virus (EBV), Cytomegalovirus (CMV), Human Herpesvirus 6 (HHV6), Human Herpesvirus 7 (HHV7) and Kaposi's Sarcoma Virus (KSV)), with high specificity, reliability, efficiency, precision (repeatability and reproducibility) and analytical sensitivity, in samples of tissue, blood, body fluids and cells in culture and any other biological source by nucleic acid amplification using the PCR technique. It should be noted that in those cell-free samples, as in the case of plasma and other body fluids, the detection of the endogenous beta-actin gene will not be possible because it naturally lacks the cellular genome.

The method described herein consists of the following steps:

1. Purification of DNA from a biological sample using a standard method such as phenol-chloroform extraction or one of the methods described in: Molecular Cloning: A Laboratory Manual by Michael R. Green and Joseph Sambrook, 2012; Current Protocols in Molecular Biology by Frederick M. Ausubel et al., 2014, or using commercial kits such as QIAamp DNA minikit (QIAGEN, Germany). Any other method could be used including those in which viral DNA is preferentially purified in cell-free samples. However, it is important to note that the selected method must be uniform among all the samples used in order to obtain homogeneous results that can be correctly interpreted.

2. Analysis of the extracted DNA using a spectrophotometric method or any other that allows quantifying it and evaluating it in terms of purity to rule out the presence of RNA, proteins, phenol or other impurities that could inhibit or interfere in any way with downstream amplification reactions.

3. Amplification of the DNA by means of quantitative, multiple, real-time PCR. The amplification reaction is carried out in two separate tubes but simultaneously in a single run, so the amplification conditions (cycling, temperatures, times, etc.) of both tubes are the same. These two reactions tested simultaneously and under the same amplification conditions will hereinafter be referred to as reaction 1 or first reaction and reaction 2 or second reaction.

The first reaction is aimed at amplifying viral genomic fragments of EBV and CMV herpesviruses and a fragment of the human endogenous beta-actin gene; the second reaction is aimed at amplifying three viral genomic fragments of herpesviruses HHV6, HHV7 and KSV. As can be seen, the first reaction, in addition to detecting viruses, aims to evaluate, through the amplification of the human endogenous beta-actin gene, the presence of inhibitors of DNA polymerase and the DNA integrity of the sample biological and thus works as an internal control of the PCR and as a control of the amplification of the sample.

Choice and Design of Initiators and Probes

To amplify the six target fragments, three pairs of primers and four probes were obtained from the literature and the rest were designed de novo for this work (Table 1). TaqMan™-type hydrolysis probes, specific for each viral target, were labeled with different fluorophores (first reaction: EBV-FAM™ (3',6'-Dihydroxy-3-oxo-3H-spiro[2-benzofuran-1,9'-xanthene]-6-carboxyl) fluorescent dye, CMV-JOE™ (4',5'-Dichloro-3',6'-dihydroxy-2',7'-dimethoxy-3-oxo-3H-spiro[2-benzofuran-1,9'-xanthene]-6-carboxyl) fluorescent dye, Beta-actin-Cy5™ (6-6-(2E)-3,3-dimethyl-2-[(2E,4E)-5-(1,3,3-trimethylindol-1-ium-2-yl)penta-2,4-dienylidene]indol-1-yl-5-carboxypentyl) fluorescent dye, second reaction: HHV6-FAM™ (3',6'-Dihydroxy-3-oxo-3H-spiro[2-benzofuran-1,9'-xanthene]-6-carboxyl) fluorescent dye, HHV7-JOE™ (4',5'-Dichloro-3',6'-dihydroxy-2',7'-dimethoxy-3-oxo-3H-spiro[2-benzofuran-1,9'-xanthene]-6-carboxyl) fluorescent dye and KSV-Cy5™ (6-6-(2E)-3,3-dimethyl-2-[(2E,4E)-5-(1,3,3-trimethylindol-1-ium-2-yl)penta-2,4-dienylidene]indol-1-yl-5-carboxypentyl) fluorescent dye).

TABLE 1

Features of initiators and probes

| | Viral/ cellular target | Viral/ cellular gene | Nucleotide sequence 5'→3' | SEQ ID NO: | ID | Long. | % GC | Tm ° C. | Product size (bp) | Source |
|---|---|---|---|---|---|---|---|---|---|---|
| First reaction | EBV | BALF5 | Forward CCCTGTTTATCCGATGGAATG | 1 | EBV_F | 19 | 63.2 | 57.8 | 90 | Kimura et. al. 1999 (6) |
| | | | Reverse CGGAAGCCCTCTGGACTTC | 2 | EBV_R | 21 | 47.6 | 53.3 | | |
| | | | Probe: FAM™(3',6'-Dihydroxy-3-oxo-3H-spiro[2-benzofuran-1,9'-xanthene]-6-carboxyl)-TGTACACGCACGAGAAATGCGCC-BHQ1a ® | 3 | EBV_S | 23 | 56.5 | 62.3 | | |
| | CMV | IE | Forward GCTACAATAGCCTCTTCCTCATCTG | 4 | CMV_F | 22 | 54.5 | 57.9 | 201 | Tanaka et. al. 2000 (20) |
| | | | Reverse GACTAGTGTGATGCTGGCCAAG | 5 | CMV_R | 25 | 48 | 56.8 | | |
| | | | Probe: JOE™(4',5'-Dichloro-3',6'-dihydroxy-2',7'-dimethoxy-3-oxo-3H-spiro[2-benzofuran-1,9'-xanthene]-6-carboxyl)-AGCCTGAGGTTATCAGTGTAATGAAGCGCC-BHQ1a ® | 6 | CMV_S | 27 | 44.4 | 58.5 | | |
| | Beta-actin | ACTB | Forward CCAGGCTAACCTCGGAAATCT | 7 | ACT_F | 21 | 52.4 | 56.6 | 225 | This work |
| | | | Reverse CATCGTCATTCCTGTGCAACT | 8 | ACT_R | 21 | 47.6 | 55.5 | | |
| | | | Probe: CY5™ (6-6-(2E)-3,3-dimethyl-2-[(2E,4E)-5-(1,3,3-trimethylindol-1-ium-2-yl)penta-2,4-dienylidene]indol-1-yl-5-carboxypentylcarbocyanine 5)-TGGGGTGCCGGCTCTCTGCT-BHQ3a ®(3-Diethylamino-5-phenylphenazium-7-diazobenzene-4"-(N-methyl-N-propylamino) | 9 | ACT_S | 20 | 70 | 66.5 | | |
| Second reaction | HHV6 | U31 | Forward CGACTCTCACCCTACTGAACGA | 10 | HHV6_F | 22 | 54.5 | 57.9 | 121 | Tanaka et. Al. 2000 (20) and this work |
| | | | Reverse GAGGCTGGCGTCGTAGTAGAA | 11 | HHV6_R | 21 | 57.1 | 58.5 | | |
| | | | Probe: FAM™ (3',6'-Dihydroxy-3-oxo-3H-spiro[2-benzofuran-1,9'-xanthene]-6-carboxyl)-AGCCACAGCAGCCATCTACATCTGTCAA-BHQ1a ® | 12 | HHV6_S | 28 | 50 | 63.3 | | |
| | HHV7 | U57 | Forward CGGAAGTCACTGGAGTAATGACAA | 13 | HHV7_F | 24 | 45.8 | 56.6 | 108 | Hara et. Al. 2002 (21) |
| | | | Reverse ATGCTTTAAACATCCTTTCTTTCGG | 14 | HHV7_R | 25 | 36 | 54.2 | | |
| | | | Probe: JOE™(4',5'-Dichloro-3',6'-dihydroxy-2',7'-dimethoxy-3-oxo-3H-spiro[2-benzofuran-1,9'-xanthene]-6-carboxyl)-CTCGCAGATTGCTTGTTGGCCATG-BHQ1a ® | 15 | HHV7_S | 24 | 54.2 | 61.1 | | |
| | KSV | LANA | Forward AGTTATGGGCGACTGGTCTG | 16 | KSV_F | 20 | 55 | 58.6 | 166 | This work |
| | | | Reverse GGATGGAAGACGAGATCCAA | 17 | KSV_R | 20 | 50 | 54.8 | | |
| | | | Probe: CY5™ (6-6-(2E)-3,3-dimethyl-2-[(2E,4E)-5-(1,3,3-trimethylindol-1-ium-2-yl)penta-2,4-dienylidene]indol-1-yl-5-carboxypentyl)-AAGTCCGTATGGGTCATTGC-BHQ3a ®(3-Diethylamino-5-phenylphenazium-7-diazobenzene-4"-(N-methyl-N-propylamino) | 18 | KSV_S | 20 | 50 | 55.1 | | |

ID: Identifier, F: Forward (sense), R: Reverse (antisense), S: Probe, Long: length of the initiator/probe. Tm: Temperature melting, % GC: guanines and cytokines percentage, bp: base pairs. FAM™ (3',6'-Dihydroxy-3-oxo-3H-spiro[2-benzofuran-1,9'-xanthene]-6-carboxyl), JOE™ (4',5'-Dichloro-3',6'-dihydroxy-2',7'-dimethoxy-3-oxo-3H-spiro[2-benzofuran-1,9'-xanthene]-6-carboxyl) and CY5™ (6-6-(2E)-3,3-dimethyl-2-[(2E,4E)-5-(1,3,3-trimethylindol-1-ium-2-yl)penta-2,4-dienylidene]indol-1-yl-5-carboxypentyl): fluorescent dyes. Black Hole Quencher®-1 BHQ1a® and Black Hole Quencher®-3 (BHQ3a® (3-Diethylamino-5-phenylphenazium-7-diazobenzene-4"-(N-methyl-N-propylamino)).

In the design of the primers to detect HHV6, KSV and beta-actin and the probes to detect KSV and beta-actin, the following programs were used: Primer-BLAST (ncbi.nlm.nih.gov/tools/primer-blast/) and Oligoanalyzer (idtdna.com/calc/analyzer).

This last program was also used to analyze different parameters of the oligonucleotides (primers and probes) previously reported (6, 20, 21) in order to homogenize them with the de novo designed oligonucleotides. Among these parameters, the most important are: melting temperature or Tm, oligonucleotide length, guanines and cytokines percentage (Table 1), as well as formation of autodimers and heterodimers. Tables 2 and 3 show the ΔG (delta G) values observed for the formation of auto-dimers and hetero-dimers respectively of the first reaction. The most negative ΔG observed in the different complementary base mating situations was considered. As can be seen, the ΔG obtained was around −9 kal/mol, the recommended reference value in the proper oligonucleotide design. Other analyzes were carried out with the oligonucleotides of the second reaction finding similar results (not shown).

For initiators, melting temperatures were in the range of 53.3° C.-58.6° C., while for probes they were between 55.1° C. and 66.5° C. The probes used were labeled with the FAM™ (3',6'-Dihydroxy-3-oxo-3H-spiro[2-benzofuran-1,9'-xanthene]-6-carboxyl), JOE™ (4',5'-Dichloro-3',6'-dihydroxy-2',7'-dimethoxy-3-oxo-3H-spiro[2-benzofuran-1,9'-xanthene]-6-carboxyl) and CY5 ™ (6-6-(2E)-3,3-dimethyl-2-[(2E,4E)-5-(1,3,3-trimethylindol-1-ium-2-yl)penta-2,4-dienylidene]indol-1-yl-5-carboxypentyl) fluorophores for the EBV, CMV and beta-actin targets respectively from the first reaction, or for the HHV6, HHV7 and KSV targets respectively from the second reaction.

TABLE 2

Deltas G obtained from the analysis of auto-dimers formation of the oligonucleotides used in the first reaction.

| Auto-dime r | ΔG (kcal/mol) |
|---|---|
| VEB_F - VEB_F | −5.12 |
| VEB_R - VEB_R | −4.64 |
| VEB_S - VEB_S | −9.89 |
| CMV_F - CMV_F | −13.19 |
| CMV_R - CMV_F | −5.7 |
| CMV_S - CMV_S | −9.89 |
| ACT_F - ACT_F | −4.67 |
| ACT_R - ACT_R | −7.05 |
| ACT_S - ACT_S | −16.03 |

F: Forward (sense), R: Reverse (antisense), S: Probe.

TABLE 3

Deltas G obtained from the analysis of formation of hetero-dimers of the oligonucleotides used in the first reaction.

| Hetero-dimer | ΔG (kcal/mol) |
|---|---|
| VEB_F - VEB_R | −8.26 |
| VEB_F - VEB_S | −3.61 |
| VEB_R - VEB_S | −3.89 |
| CMV_F - CMV_R | −6.21 |
| CMV_F - CMV_S | −6.21 |
| CMV_R - CMV_S | −8.2 |
| ACT_F - ACT_R | −6.62 |
| ACT_F - ACT_S | −6.68 |
| ACT_R - ACT_S | −5.09 |
| VEB_F - CMV_F | −6.21 |
| VEB_F - CMV_R | −8.19 |
| VEB_F - CMV_S | −6.24 |
| VEB_R - CMV_F | −5.02 |
| VEB_R - CMV_R | −6.59 |
| VEB_R - CMV_S | −4.67 |
| VEB_S - CMV_F | −6.21 |
| VEB_S - CMV_R | −4.26 |
| VEB_S - CMV_S | −9.89 |
| ACT_F - ACT_F | −7.81 |
| ACT_F - ACT_R | −9.83 |
| ACT_F - ACT_S | −6.78 |
| ACT_R - ACT_F | −6.59 |
| ACT_R - ACT_R | −10.02 |
| ACT_S - ACT_S | −6.53 |
| ACT_S - ACT_F | −7.81 |
| ACT_S - ACT_R | −6.68 |
| ACT_S - ACT_S | −6.44 |
| ACT_F - CMV_F | −6.62 |
| ACT_F - CMV_R | −10.37 |
| ACT_F - CMV_S | −11.36 |
| ACT_R - CMV_F | −5.09 |
| ACT_R - CMV_R | −3.42 |
| ACT_R - CMV_S | −6.95 |
| ACT_S - CMV_F | −6.21 |
| ACT_S - CMV_R | −7.81 |
| ACT_S - CMV_S | −7.81 |

F: Forward (sense), R: Reverse (antisense), S: Probe.

Cloning and Sequencing of Viral Gene Fragments

For the quantification of viral load, standard curves with serial dilutions of plasmids containing viral gene fragments were used, which were obtained from different sources and cloned in commercial vectors as described below.

The commercial cell line Raji (Burkitt lymphoma, EBV+, American Type Culture Collection (ATCC) CCL-86) was used for EBV. For CMV, a supernatant from a primary culture of infected human foreskin fibroblasts (kindly donated by Dr. José Arellano-Galindo, Hospital Infantil de México Federico Gómez) was used. For HHV6, the MOLT3 T cell line (ATCC-CRL-1552) permissive to infection was used, which was infected in the laboratory with commercial viral particles (ATCC-VR1467), the supernatant of the infection was used to obtain HHV6. For HHV7, DNA from the B5 strain donated by Dr. Tzindilú Molina-Muñoz (Centro Médico Nacional SXXI, Instituto Mexicano del Seguro Social) was used. For KSV, the culture supernatant of the cell line BCP-1 (ATCC-CRL-2294) positive to KSV was used. MOLT3, Raji and BCP-1 cell lines were cultured in RPMI (Gibco) medium supplemented with 10% (MOLT3, Raji) and 20% (BCP-1) of fetal bovine serum (Gibco) and antibiotic-antifungal 1× (Gibco).

DNA from the above cell lines or supernatant was purified using the commercial QIAamp DNA Mini Kit (Qiagen) according to the manufacturer's instructions. The concentration and quality of the recovered DNA was estimated by measuring the absorbance in a nanodrop spectrophotometer (Thermo Fisher Scientific) at an optical density of 280 or from the 260/280 ratio.

DNA recovered from the supernatants or cell lines as appropriate for each virus was used in endpoint PCR amplification of viral gene fragments using the primers described in Table 1. PCR products were purified from agarose gels (Sigma-Aldrich) 1% stained with ethidium bromide (Sigma-Aldrich) using the commercial QIAquick extraction kit (Qiagen). The PCR product of the herpesvirus gene fragments was ligated to the commercial vector pGEM-T Easy (Promega) at the Eco RI site as specified by the manufacturer. Competent bacteria (*E. coli* strain DH5a) were generated, which were transformed with the ligation products in independent experiments for each of the viruses. Successfully transformed clones were doubly selected by growth in ampicillin and the white coloration obtained in cloning systems using the principle of α-complementation by IPTG and x-gal (FIG. 1).

Figure 2:
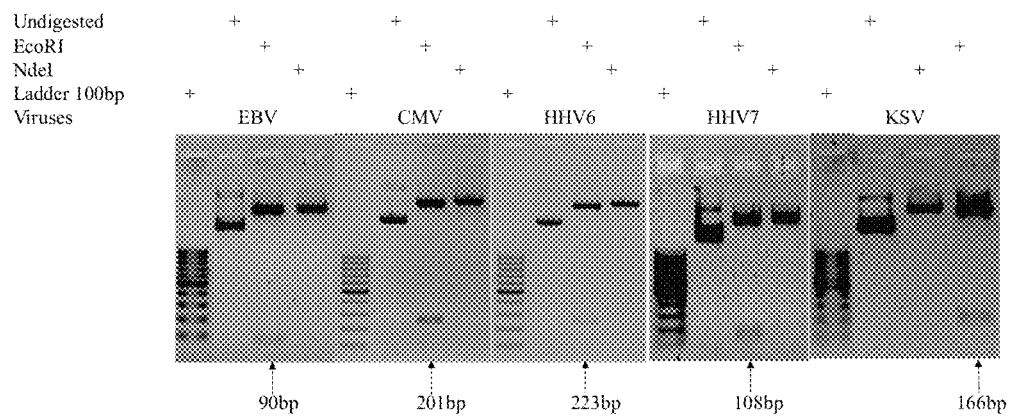
FIG. 2. 1% agarose gel shows the digestion of plasmid DNA from each of the selected clones of successfully transformed bacteria. On each gel: The first lane shows the 100 bp molecular weight marker (marker with increments every 100 base pairs). In the following lanes the plasmid is shown undigested or digested with the EcoRI enzymes (releases the viral fragment from the plasmid) and NdeI (linearizes the plasmid) as indicated.

From the transformed bacteria 10 successfully transformed clones (white) were isolated and seeded in LB (Luria-Bertani) and LBA (Luria-Bertani-agar) medium, the plasmid DNA was purified with the commercial Pure Link Quick Plasmid Miniprep kit (Invitrogen). The plasmid was digested with the restriction enzymes EcoRI (insert release) and NdeI (linearizes the plasmid). The reaction was visualized by means of a 2% agarose gel (FIG. 2).

The cloned viral fragments were sequenced by direct automated sequencing of the sense and antisense strands at the UNAM Institute of Cell Physiology. The identity of the viral sequences was confirmed by Blast analysis using the Standard Nucleotide BLAST program of the Basic Local Alignment Search Tool (22).

Assembly of the Real Time Multiplex PCR

The described method uses two multiplex PCR reactions that are run on the same equipment simultaneously. As mentioned above, the first reaction is aimed at amplifying viral genomic fragments of EBV and CMV herpesviruses and a fragment of the endogenous human beta-actin gene; the second reaction is aimed at amplifying three viral genomic fragments of herpesviruses HHV6, HHV7 and KSV.

Initiators Specificity

Figure 3:
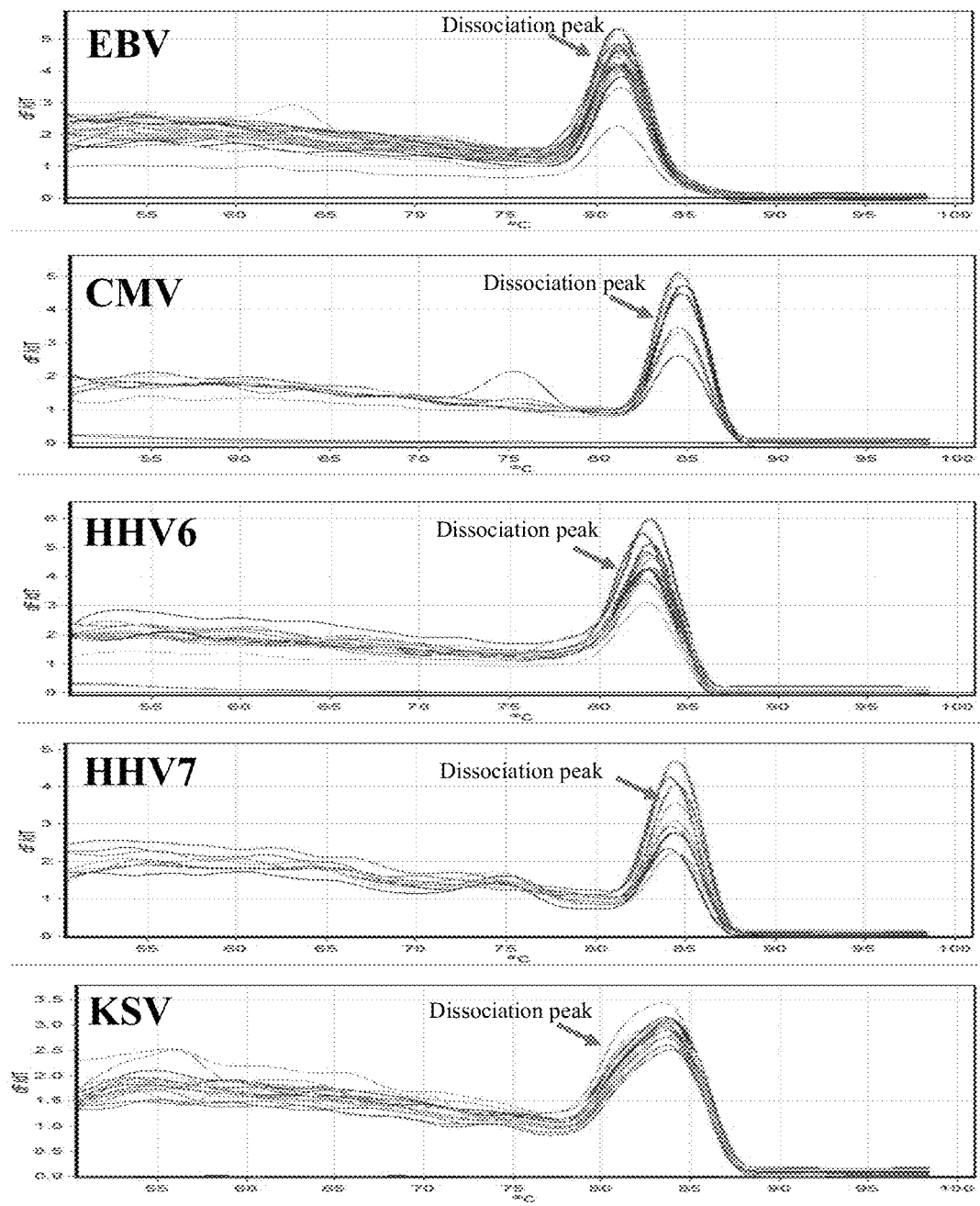
FIG. 3. Dissociation curves or MELT of the five viral plasmids, the dissociation temperature is observed on the "X" axes and the fluorescence on the "Y" axes, a perfectly marked dissociation peak isv distinguished between the 80 and 85° C. (red arrow).

First, Syber Green-based PCR reactions were carried out in simple format. Standard curves were performed with serial dilutions ($10^6$ to $10^1$ molecules) of the control plasmids containing the viral genomic fragments. To each reaction tube, in addition to the plasmid DNA, 100 ng of DNA from a negative human cell line were added to all the viruses under study (MOLT3). Each reaction was run individually using at the end of the reaction adding a dissociation curve or MELT curve to determine the specificity of the initiators. FIG. 3 shows the five dissociation curves obtained, observing that a single perfectly marked dissociation peak between 80 and 85° C. is distinguished for each amplicon, which indicated that the designed primers do not amplify nonspecific fragments in a background of human genomic DNA.

Reliability of Standard Curves

Figure 4:
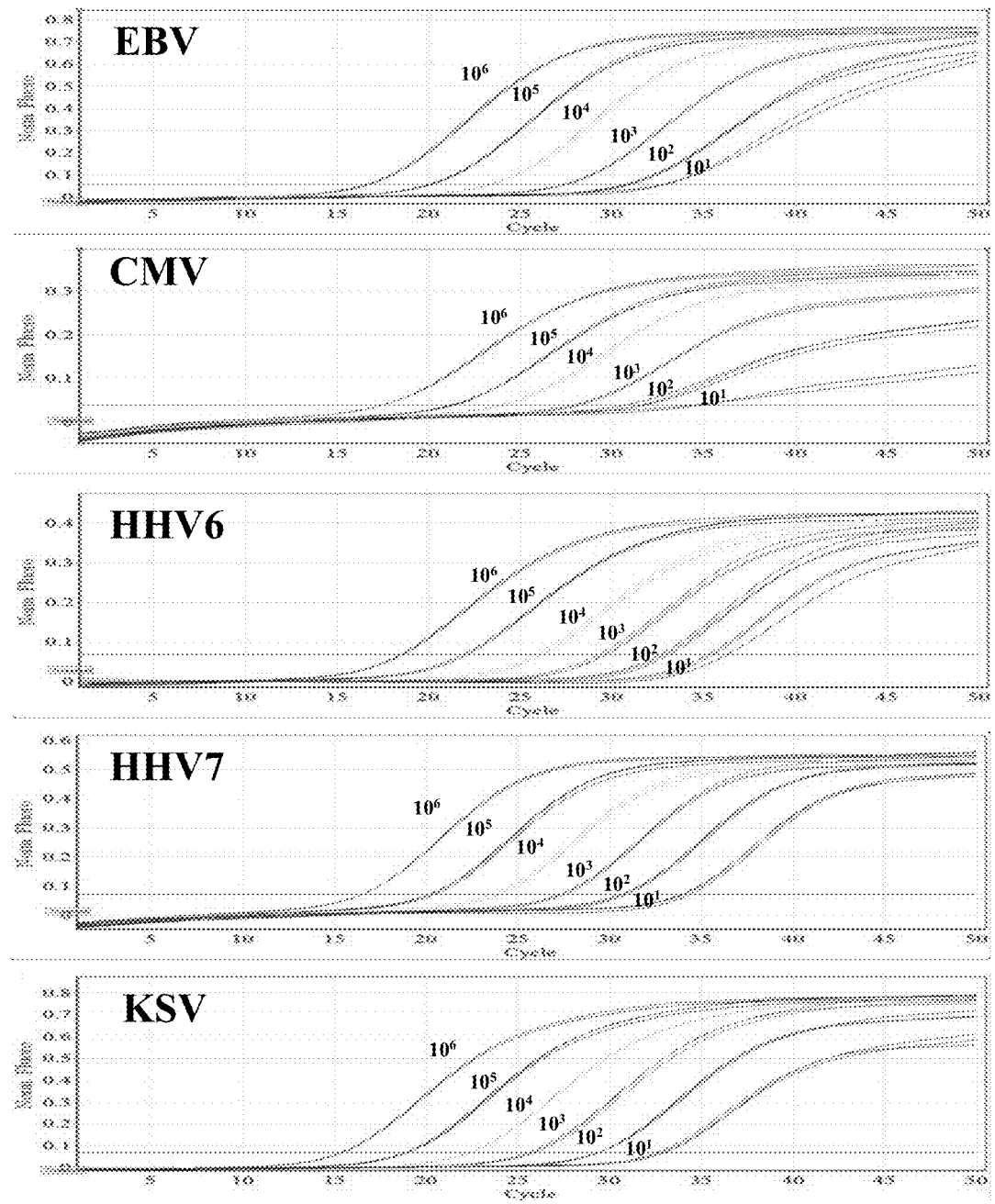
FIG. 4. Fluorescence curves of the five plasmids. Each standard curve was performed with serial dilutions of $10^6$ (red), $10^5$ (blue), $10^4$ (yellow), $10^3$ (green), $10^2$ (purple), and $10^1$ (black) plasmid molecules containing the viral gene fragments. Each point on the curve was run in triplicate. Amplification cycles are plotted on the "X" axes and fluorescence on the "Y" axes. Great homogeneity is observed in the curves and the determination coefficients ($R^2$) were adequate, ranging between 0.98825 and 0.99609 (see Table 4).

Subsequently, the PCRs were performed individually, but now using the fluorescently labeled probes specific for each target. Each standard curve was performed with serial dilutions ($10^6$, $10^5$, $10^4$, $10^3$, $10^2$, and $10^1$) of the control plasmid (FIG. 4).

Table 4 shows the values of the average coefficients of determination ($R^2$) obtained from at least 3 repetitions of each of the reactions. $R^2$ values greater than 0.98 were obtained, which indicates that the standard curves are highly reliable so that the number of viral copies present in a test sample can be predicted from them.

TABLE 4

Determination coefficients ($R^2$) obtained for each of the reactions.

| Virus-Gene (Fluorophore-Quencher) | ($R^2$) |
|---|---|
| VEB-BALF (FAM-BHQ1) | 0.98825 |
| CMV-IE (HEX-BHQ1) | 0.98928 |
| HHV6-U31 (FAM-BHQ1) | 0.99248 |
| HHV7-U57 (HEX-BHQ1) | 0.99609 |
| KSV-LANA (CY5-BHQ2) | 0.99134 |

Amplification conditions of multiplex PCR

The QuantiTect Multiplex PCR NoRox Kit (Qiagen) reaction mixture, a ready-to-use reagent and specially designed for multiple reactions, was used. The primers and probes were commercially synthesized (DNA Synthetic S.A.P.I. de C.V.). The reaction mixtures were brought to a final volume of 20 μl each. Each reaction tube contained reaction mixture, primers, probes, plasmid DNA and also human genomic DNA (100 ng) from a cell line negative for all viruses under study (MOLT3). This background DNA served to homogenize the DNA concentrations present in a test biological sample in relation to the concentration present in each tube of the standard curves. The reagents, their volumes and concentrations used are listed in Table 5.

TABLE 5

Reagents used in multiplex PCRs.

| | REACTION 1 | | | REACTION 2 | |
|---|---|---|---|---|---|
| Reagent | Final concentration | Volume (μl) | Reagent | Final concentration | Volume (μl) |
| Master mix | 1x | 10 | Master mix | 1x | 10 |
| VEB_F | 250 nM | 0.5 | HHV6 F | 250 nM | 0.5 |
| VEB_R | 250 nM | 0.5 | HHV6 R | 250 nM | 0.5 |
| VEB_S | 125 nM | 0.25 | HHV6 S | 125 nM | 0.25 |
| CMV_F | 250 nM | 0.5 | HHV7 F | 250 nM | 0.5 |
| CMV_R | 250 nM | 0.5 | HHV7 R | 250 nM | 0.5 |
| CMV_S | 125 nM | 0.25 | HHV7 S | 125 nM | 0.25 |
| ACT_F | 125 nM | 0.25 | LANA F | 250 nM | 0.5 |
| ACT_R | 125 nM | 0.25 | LANA R | 250 nM | 0.5 |
| ACT_S | 62.5 nM | 0.125 | LANA S | 125 nM | 0.25 |
| Plasmid DNA | * | 3 | Plasmid DNA | * | 3 |

TABLE 5-continued

Reagents used in multiplex PCRs.

| REACTION 1 | | | REACTION 2 | | |
|---|---|---|---|---|---|
| Reagent | Final concentration | Volume (μl) | Reagent | Final concentration | Volume (μl) |
| ADN background | 100 ng/μl | 1 | ADN background | 100 ng/μl | 1 |
| RNase-free H₂O | — | 2.875 | RNase-free H₂O | — | 2.875 |

* The plasmid DNA concentration was variable depending on the number of copies of each point of the curve but it was always adjusted to 3 μl.

Amplification conditions were chosen according to the design and features of primers, probes and amplification products and were based on conditions already reported for multiplex PCR (15). A "hold" cycle was added prior to amplification cycling to activate the UDG (Uracil-DNA Glycosylase) system included in the reaction mixture used (QuantiTect Multiplex PCR NoRox Kit, Qiagen), which eliminates carry-over contamination. In such a way that the amplification conditions for the two reactions run simultaneously were as follows (Table 6):

TABLE 6

Amplification conditions

| Step (process) | Pre-hold (UDG) | Hold (denaturation) | Cycling (denaturation + alignment and extension) |
|---|---|---|---|
| Temperature/time | 52° C./2.5 min | 95° C./15 min | 95° C./15 sec + 60° C./1 min |
| No. of cycles | 1x | 1x | 50x |

Correlations Between Multiplex Reactions and Individual Reactions

The reactions were then run in multiple format (triplex) according to the conditions and blanks previously described. At least 5 standard curves were made per viral target and each point on the curve was run in triplicate.

Figure 5:
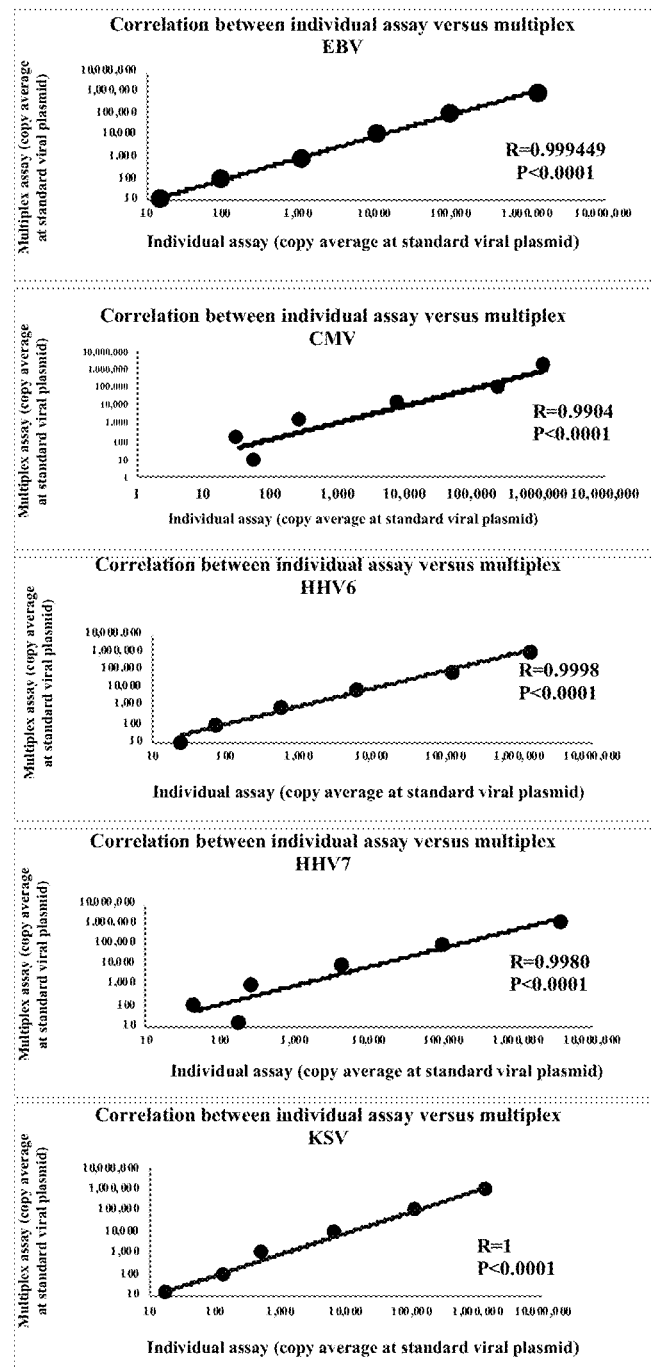
FIG. 5. Correlation graphs of the number of copies observed in the standard curves comparing the individual reaction versus the multiple reaction. For each of the simple and multiple reactions, three assays were performed in triplicate, from which 9 measurements were obtained for each point on the standard curve (54 per reaction), which were averaged and compared by Pearson's correlation analysis (R). The copies of the viral plasmid obtained in the individual reaction are plotted on the "X" axis and the copies of the viral plasmid obtained in the multiplex reaction are plotted on the "Y" axis. According to the R coefficients close to 1 that were obtained, simple reactions have a high correlation with multiple reactions.

To know the efficiency of multiplex reactions (triplex) in relation to the reactions run individually, correlation analysis was performed. For each point on a given curve, the average number of viral copies obtained in both formats was compared. FIG. 5 shows the obtained correlation graphs. The viral load values obtained in the individual reaction are plotted on the "X" axis and the viral load values obtained in the multiplex reaction on the "Y" axis. As can be seen for each of the five amplification reactions, R coefficients very close to 1 were obtained, this indicates a high correlation between the number of DNA copies determined by the individual reactions versus the multiplex reactions, which allows us to conclude that the use of multiple PCR maintained the same efficiency as the individual counterpart.

Analytical Sensitivity and Reproducibility of Multiplex PCRs Reactions

The analytical sensitivity of multiplex PCR reactions is expressed by the detection limit (Table 7). The detection limit is the minimum copy number that can be reliably amplified and is determined from the average of the observed minimum copy number plus three times its standard deviation (23). In this work, the analytical sensitivity was determined from the lower point ($10^1$) run in triplicate of 17 independently run standard curves (N=51). As can be seen in Table 7, the detection limits varied for each virus with a range of 21.33 to 33.28 for EBV and HHV7 respectively.

The reproducibility of multiplex assays is expressed with the coefficient of variation (Table 8), which expresses the percentage relationship between the standard deviation and the mean of a data set and is calculated with the following formula: $CV=(\sigma/\bar{x})*100$. An adequate variation coefficient must be below 5% (95% reliability). Both in the intra-assay analysis (one assay run in triplicate for each point on the standard curve, N=3) and in the inter-assay analyzes (three assays run in triplicate for each point on the standard curve, N=9) the variation coefficients were less than 5%, which indicated that the reactions were highly reproducible (Tables 8 and 9).

TABLE 7

Analytical sensitivity of each PCR.

| PCR | Detection limit (number of copies) |
|---|---|
| VEB reaction | 21.33 |
| CMV reaction | 24.29 |
| HHV6 reaction | 21.53 |
| HHV7 reaction | 33.28 |
| KSV reaction | 29.63 |

TABLE 8

Intra-assay variation coefficients

| Standard curve point | Variation coefficient (%) | | | | |
|---|---|---|---|---|---|
| (number of plasmid copies) | VEB | CMV | HHV6 | HHV7 | KSV |
| $1 \times 10^6$ | 0.31 | 0.73 | 0.44 | 0.54 | 0.31 |
| $1 \times 10^5$ | 0.77 | 2.93 | 0.91 | 0.44 | 0.31 |
| $1 \times 10^4$ | 0.96 | 1.64 | 0.93 | 0.69 | 1.27 |
| $1 \times 10^3$ | 1.43 | 3.30 | 0.50 | 1.05 | 0.67 |
| $1 \times 10^2$ | 1.82 | 1.65 | 0.43 | 0.87 | 0.69 |
| $1 \times 10^1$ | 2.54 | 3.55 | 0.65 | 1.43 | 1.19 |

TABLE 9

Inter-assay Variation Coefficients

| Standard curve point | Variation coefficient (%) | | | | |
|---|---|---|---|---|---|
| (number of plasmid copies) | VEB | CMV | HHV6 | HHV7 | KSV |
| $1 \times 10^6$ | 0.96 | 3.12 | 1.89 | 0.49 | 0.66 |
| $1 \times 10^5$ | 1.77 | 2.89 | 1.21 | 0.76 | 0.96 |
| $1 \times 10^4$ | 1.49 | 2.94 | 1.33 | 0.91 | 1.13 |
| $1 \times 10^3$ | 1.75 | 2.35 | 1.95 | 0.85 | 0.57 |

TABLE 9-continued

Inter-assay Variation Coefficients

| Standard curve point (number of plasmid copies) | Variation coefficient (%) | | | | |
|---|---|---|---|---|---|
| | VEB | CMV | HHV6 | HHV7 | KSV |
| $1 \times 10^2$ | 1.88 | 2.53 | 1.63 | 0.69 | 1.09 |
| $1 \times 10^1$ | 2.09 | 3.87 | 0.72 | 2.67 | 2.60 |

Example

This example involves the analysis of herpesviruses 4 (EBV), 5 (CMV), 6 (HHV6), 7 (HHV7) and 8 (KSV) in pediatric post-transplant patients.

The Hospital Infantil de México Federico Gómez (HIMFG) is one of the main transplant centers in our country, it has three solid organ transplant programs: kidney, liver and heart (24).

Viral loads of five herpesviruses (EBV, CMV, HHV6, HHV7, and KSV) were determined in total peripheral blood leukocytes from 27 pediatric patients undergoing kidney or liver transplantation. 349 samples were collected in a follow-up of 4-12 months. The following results were found: 34 samples showed a point whose viral load exceeded any of the five established clinical thresholds; 16 of them presented sustained high viral loads in contiguous times, with HHV7 being the virus that most frequently exceeded the established threshold. In conclusion, the method developed in this work was useful in the detection of the 5 herpesviruses in a group of post-transplantation pharmacologically immunosuppressed patients.

Materials and Methods

Patients and Biological Samples

Twenty-seven patients undergoing solid organ transplantation (liver transplant N=6, kidney transplant N=21) performed at the HIMFG between February and November 2016 were included. 349 peripheral blood samples were collected (mean=13 samples per patient), which were taken during the following 4-12 months post-transplant with a periodicity of 15 to 30 days.

The protocol was approved by the HIMFG Scientific, Ethical and Biosafety Committees (Protocol Record: HIM-2016-021). The parents of the patients and patients (older than 10 years) who agreed to participate in the study signed consent letters and informed consent, respectively.

DNA Purification

Peripheral blood samples were collected in Vacutainer tubes with EDTA as anticoagulant (Becton-Dickinson). Plasma was separated from cell contents by centrifugation (10 min., 35000 rpm) and immediately frozen at −70° C. Leukocytes were isolated by lysis of erythrocytes using EL buffer (Qiagen), 3 washes with 1× PBS buffer were performed. DNA was purified from 1-4×106 cells using the commercial QIAamp DNA Mini Kit (Qiagen) according to the manufacturer's instructions. In each purification, the RNAase reagent (100 mg/ml) (Qiagen) was used to eliminate RNA contamination. The amount and purity of the DNA obtained was evaluated by absorbance readings at 260 and 260/280 respectively using a nanodrop 2000 spectrophotometer (Thermo Fisher Scientific). DNA samples were frozen until later use.

Viral Load Evaluation by Multiplex Quantitative Real-Time PCR

The viral load of the five herpesviruses of interest was determined in the 349 leukocyte samples from 27 patients in the post-transplant period. Two multiplex quantitative real-time PCR reactions (two tubes) were performed simultaneously using TaqMan™-type hydrolysis probes, specific for each viral target, labeled with different fluorophores (first reaction: EBV-FAM™ (3',6'-Dihydroxy-3-oxo-3H-spiro[2-benzofuran-1,9'-xanthene]-6-carboxyl) fluorescent dye, CMV-JOE™ (4',5'-Dichloro-3',6'-dihydroxy-2',7'-dimethoxy-3-oxo-3H-spiro[2-benzofuran-1,9'-xanthene]-6-) fluorescent dye, Beta-actin-Cy5™ (6-6-(2E)-3,3-dimethyl-2-[(2E,4E)-5-(1,3,3-trimethylindol-1-ium-2-yl)penta-2,4-dienylidene]indol-1-yl-5-carboxypentyl) fluorescent dye, second reaction: HHV6-FAM™ (3',6'-Dihydroxy-3-oxo-3H-spiro[2-benzofuran-1,9'-xanthene]-6-carboxyl) fluorescent dye, HHV7-JOE™ (4',5'-Dichloro-3',6'-dihydroxy-2',7'-dimethoxy-3-oxo-3H-spiro[2-benzofuran-1,9'-xanthene]-6-carboxyl) fluorescent dye and KSV-Cy5™ (6-6-(2E)-3,3-dimethyl-2-[(2E,4E)-5-(1,3,3-trimethylindol-1-ium-2-yl)penta-2,4-dienylidene]indol-1-yl-5-carboxypentyl) fluorescent dye). The first reaction was aimed at detecting the human endogenous beta-actin gene and EBV and CMV herpesviruses. The second reaction was aimed at detecting HHV6, HHV7 and KSV herpesviruses. Quantification was performed from standard curves constructed with serial dilutions ($10^6$-$10^1$) of plasmids containing viral genomic fragments and 100 ng of DNA from a human cell line negative for all viruses under study (MOLT3). This last DNA was used as background to homogenize the tempering concentrations of the test samples versus the standard curves. The QuantiTect multiplex PCR kit (Qiagen) 1× reaction mixture was used. All primers were brought to a final concentration of 250 nM and all probes were brought to a final concentration of 125 nM, with the exception of beta-actin-specific primers and probe, which used a final concentration of 125 nM and 62.5 nM respectively.

Results

Patients and Biological Samples 27 patients were included in the study, 21 were kidney transplant patients and 6 liver transplant patients. Transplant ages ranged from 4 to 17 years, with a median of 14 years, 56% of patients were children. Follow-up was carried out for 4-12 months collecting a total of 349 samples, with a periodicity of 15 days (±6 days) the first three months and 30 days (±12 days) from the third month. The variation of +6 and +12 days occurred due to the fact that only a blood sample was taken when the attending physician indicated that other studies should be carried out, in no case was a specific appointment requested for the sampling of this protocol. Table 10 summarizes the clinical data of the patients included in the study.

TABLE 10

Clinical-demographic data of the patients included in the study (N = 27).

| | |
|---|---|
| Transplant type | Hepatic: 22% (n = 6) |
| | Kidney: 78% (n = 21) |
| Transplant age | 4-17 years (Median = 14 years) |
| Sex | 44% Female |
| | 56% Male |
| Transplant type | 69% Cadaveric |
| | 31% Related living donor |

TABLE 10-continued

Clinical-demographic data of the patients included in the study (N = 27).

| | |
|---|---|
| Pre-transplant diagnosis* | Hepatic Transplant:<br>Bile duct atresia (n = 3, 50%)<br>Fulminant hepatitis (n = 1, 16.6%)<br>Liver fibrosis (n = 1, 16.6%)<br>Hepatitis neonatal (n = 1, 16.6%)<br>Kidney Transplant:<br>Chronic Kidney disease (n = 8, 38%)<br>Unknown etiology (n = 8, 38%)<br>Other causes (n = 5, 24%) |

Determination of Clinical Thresholds

Based on the analyzed literature (4-9) and the experience of HIMFG clinicians, clinical thresholds were established for each of the herpesviruses analyzed (Table 11). It is important to mention that for the HHV6, HHV7 and KSV viruses, the information obtained from the literature was very scarce.

TABLE 11

Clinical thresholds of the five herpesviruses under study.

| Virus | Clinical threshold (viral copies/µg ADN) |
|---|---|
| VEB | 500 |
| CMV | 500 |
| HHV6 | 200 |
| HHV7 | 200 |
| KSV | 100 |

Determination of Viral Loads in Patient Samples

Figure 6:
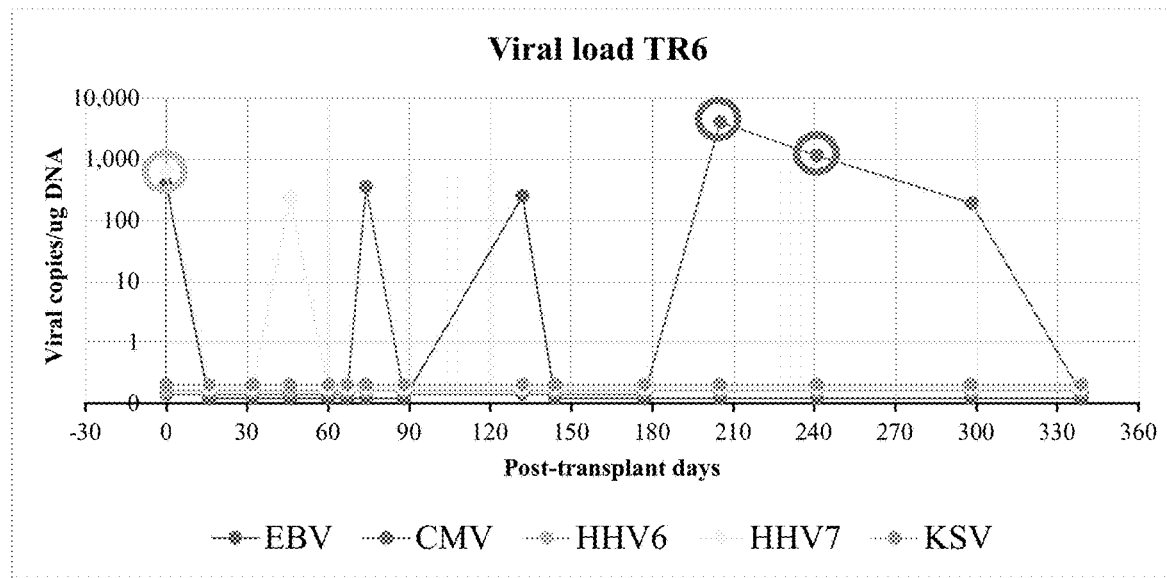
FIG. 6. Graph of the viral loads of the five herpesviruses from patient TR6 (Sixth kidney transplant patient included in the protocol). Post-transplant days are plotted on the "X" axis and the viral load in viral copies per μg of DNA found in each sample analyzed is plotted on the "Y" axis. The plotted points represent samples whose viral loads exceeded the detection limits (Table 5), their color defines the herpesvirus to which it belongs: EBV (blue), CMV (red), HHV6 (green), HHV7 (yellow) and KSV (gray). However, only those points with a circle represent samples whose viral loads exceeded some clinical threshold (Table 9).

The viral loads of the five herpesviruses were determined in the 27 analyzed patients. Table 12 exemplifies the results obtained for one of the kidney transplant patients with a 12-month follow-up. The viral loads of the five herpesviruses analyzed in each of the samples belonging to the patient with TR6 code (sixth kidney transplant patient to be part of the protocol) are shown, 14 samples were analyzed during follow-up: time 0-time 13. In FIG. 6, the viral load results are plotted as a function of the follow-up time.

TABLE 12

Viral loads of patient TR6.

| Sample | Post-transplant days | VEB (viral copies/µg ADN) | CMV (viral copies/µg ADN) | HHV6 (viral copies/µg ADN) | HHV7 (viral copies/µg ADN) | KSV (viral copies/µg ADN) |
|---|---|---|---|---|---|---|
| 0 | 0 | 400 | 0 | 0 | 620 | 0 |
| 1 | 16 | 0 | 0 | 0 | 0 | 0 |
| 2 | 32 | 0 | 0 | 0 | 0 | 0 |
| 3 | 46 | 0 | 0 | 0 | 0 | 0 |
| 4 | 60 | 0 | 0 | 0 | 0 | 0 |
| 5 | 74 | 0 | 350 | 0 | 0 | 0 |
| 6 | 88 | 0 | 0 | 0 | 0 | 0 |
| 7 | 132 | 250 | 0 | 0 | 0 | 0 |
| 8 | 144 | 0 | 0 | 0 | 0 | 0 |
| 9 | 177 | 0 | 0 | 0 | 0 | 0 |
| 10 | 205 | 0 | 4010 | 0 | 0 | 0 |
| 11 | 241 | 0 | 1130 | 0 | 0 | 0 |
| 12 | 278 | 0 | 0 | 0 | 0 | 0 |
| 13 | 298 | 0 | 0 | 0 | 0 | 0 |
| 14 | 339 | 0 | 0 | 0 | 0 | 0 |

In bold, the points whose viral loads exceeded the clinical threshold established for a given virus are highlighted.

Analysis of Viral Loads

The first viral load analysis criterion was the detection limit, all viral loads below the reliable detection limits indicated in Table 5 were considered negative; the rest of the charges were considered positive and were analyzed as described below.

Viral Loads that Exceeded Established Clinical Thresholds

Figure 9:
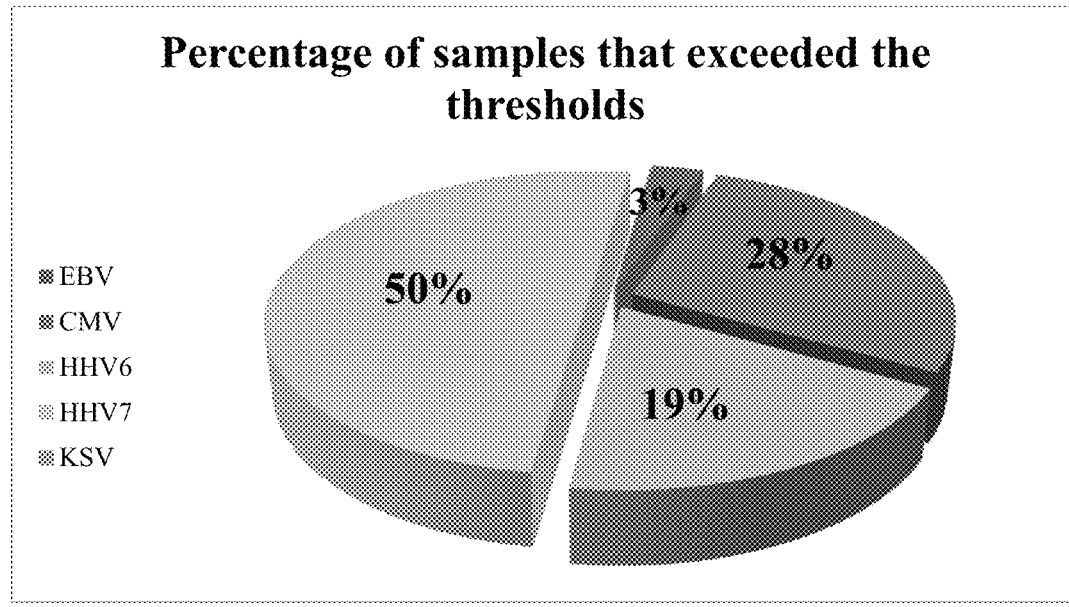
FIG. 9. Graph that summarizes the percentages of virus-positive samples.

Of the 349 samples analyzed, 34 exceeded the established clinical thresholds for at least one of the five viruses. For example, the graph in FIG. 6 marks three points that exceeded some threshold in colored circles, the yellow circle indicates a point whose viral load exceeded the threshold for the HHV7 virus, and the two red circles indicate two points with viral loads that exceeded the threshold for the CMV virus. The other points without a circle, although positive, did not exceed the clinical thresholds established as relevant and are not considered of clinical importance in this analysis. As described for TR6 (FIG. 6), the rest of the patients were analyzed. Of the 27 patients analyzed, 13 did not show points whose viral loads exceeded any of the five thresholds, so they were not included in Table 13, which summarizes the results obtained. This Table shows the patients who presented at least one point at which the viral load exceeded the established clinical threshold for the different herpesviruses. It was found that 50% of the points had viral loads that exceeded the established threshold for HHV7 virus, followed by CMV and HHV6 (FIG. 9).

TABLE 13

Samples in which the established clinical thresholds were exceeded.

| Patient | Analyzed samples | Total number of samples in which the clinical threshold was exceeded | Viruses in which clinical thresholds were exceeded | | | | |
|---|---|---|---|---|---|---|---|
| | | | VEB | CMV | HHV6 | HHV7 | KSV |
| TRI | 17 | 2 | — | — | — | 2 | — |
| TR2 | 14 | 4 | — | 1 | 1 | 2 | — |
| TR5 | 15 | 2 | — | 1 | — | 1 | — |
| TR6 | 16 | 3 | — | 2 | — | 1 | — |
| TRIO | 14 | 1 | — | — | — | 1 | — |
| TR13* | 13 | 1 | 1 | — | 1 | 1 | — |
| TR14 | 13 | 1 | — | 1 | — | — | — |
| TR15 | 13 | 7 | — | — | 1 | 6 | — |
| TR16 | 11 | 1 | — | — | 1 | — | — |
| TR17 | 12 | 5 | — | 2 | 2 | 1 | — |
| TR22* | 7 | 2 | — | 2 | — | — | — |
| TH3 | 17 | 1 | — | 1 | — | — | — |
| TH5 | 15 | 1 | — | — | 1 | — | — |
| TH6 | 14 | 3 | — | — | — | 3 | — |
| total | 349 | 34 | 1 | 10 | 7 | 18 | 0 |

TR: kidney transplant, TH: liver transplant.
*Sample TR13 presented co-infection with EBV, HHV6 and HHV7 in the same sample, while in the rest of the samples, infections were detected in different samples.
*The patient code is not consecutive due to the elimination of some patients.

Patients Who Sustained Viral Loads that Exceeded Clinical Thresholds

Figure 7:
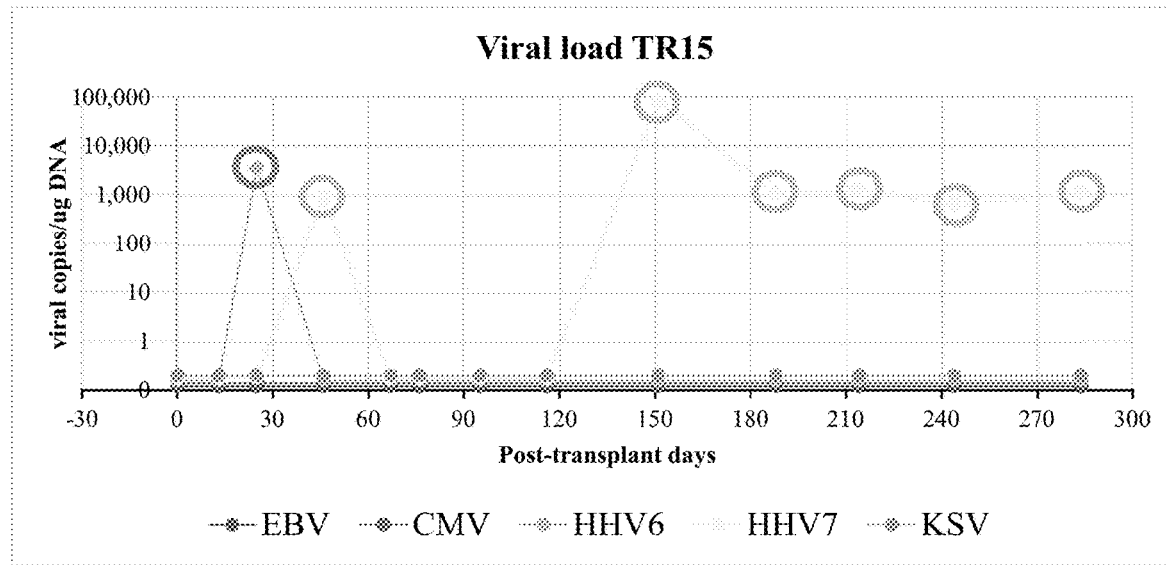
FIG. 7. Graph of the viral loads of the five herpesviruses from patient TR15 (fifteenth kidney transplant patient included in the protocol). Post-transplant days are plotted on the "X" axis and the viral load in viral copies per μg of DNA found in each sample analyzed is plotted on the "Y" axis. The plotted points represent samples whose viral loads exceeded the detection limits (Table 5), their color defines the herpesvirus to which the point belongs: EBV (blue), CMV (red), HHV6 (green), HHV7 (yellow) and KSV (gray). However, only those points with a circle represent samples whose viral loads exceeded some clinical threshold. This graph exemplifies the patients whose viral loads remained above the same threshold point in a continuous period of time, in this case five samples are observed whose viral loads exceeded the clinical threshold established for HHV7 continuously from day 151 and until day 284 (more than 4 months with a sample analyzed per month).

Of the 27 patients analyzed, in 6, at least two samples were observed whose viral loads were maintained above the same threshold point in a continuous period of time. Table 14 summarizes the data of the 6 patients, two groups are clearly distinguished, those that exceed the threshold for CMV and those that exceed the threshold for HHV7. The graph in FIG. 7 exemplifies these results with patient TR15, who presented 5 samples whose viral loads exceeded the threshold for HHV7 virus continuously from day 151 to day 284 (See also Table 15).

TABLE 14

Patients who sustained viral loads that exceeded clinical thresholds.

| Patient | Number of samples * | Involved virus |
|---|---|---|
| TR6 | 2 | CMV |
| TR17 | 2 | CMV |
| TR22 | 2 | CMV |
| TR2 | 2 | HHV7 |
| TH6 | 3 | HHV7 |
| TR15 | 5 | HHV7 |

* Refers to the number of samples that exceeded the clinical threshold

TABLE 15

Viral Loads of Patient TR15

| Sample | Post-transplant days | VEB (viral copies/µg ADN) | CMV (viral copies/µg ADN) | HHV6 (viral copies/µg ADN) | HHV7 (viral copies/µg ADN) | KSV (viral copies/µg ADN) |
|---|---|---|---|---|---|---|
| 0 | 0 | 0 | 0 | 0 | 0 | 0 |
| 1 | 13 | 0 | 0 | 0 | 0 | 0 |
| 2 | 25 | 0 | 0 | 3580 | 0 | 0 |
| 3 | 46 | 0 | 0 | 0 | 930 | 0 |
| 4 | 67 | 0 | 0 | 0 | 0 | 0 |
| 5 | 76 | 0 | 0 | 0 | 0 | 0 |
| 6 | 95 | 0 | 0 | 0 | 0 | 0 |
| 7 | 116 | 0 | 0 | 0 | 0 | 0 |
| 8 | 151 | 0 | 0 | 0 | 82470 | 0 |
| 9 | 188 | 0 | 0 | 0 | 1100 | 0 |
| 10 | 214 | 0 | 0 | 0 | 1300 | 0 |
| 11 | 244 | 0 | 0 | 0 | 600 | 0 |
| 12 | 284 | 0 | 0 | 0 | 1130 | 0 |
| CLINICAL THRESHOLD | | 500 | 500 | 200 | 200 | 100 |

Co-Infections with More than One Herpesvirus

Figure 8:
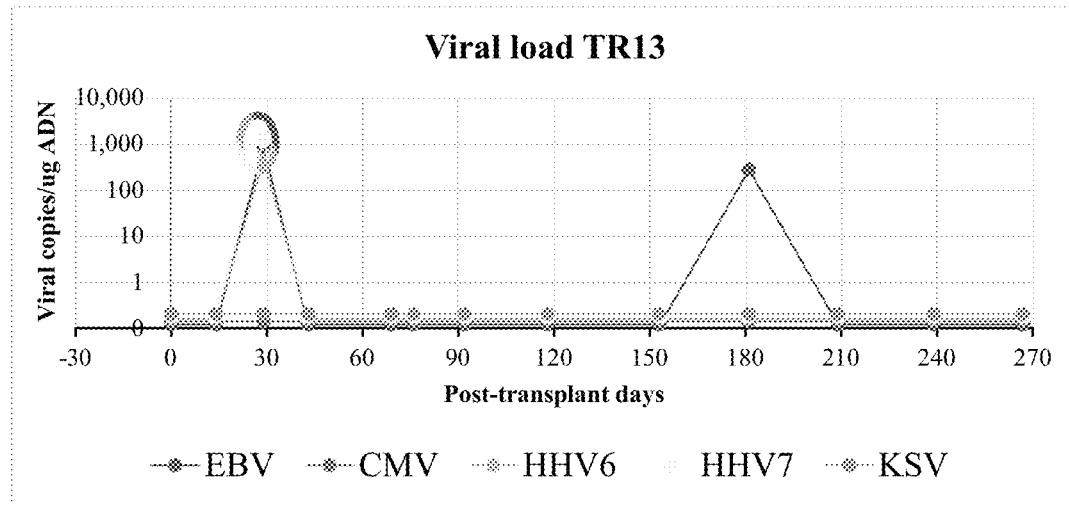
FIG. 8. Graph of the viral loads of the five herpesviruses from patient TR13 (thirteenth kidney transplant patient included in the protocol). Post-transplant days are plotted on the "X" axis and the viral load in viral copies per μg of DNA found in each sample analyzed is plotted on the "Y" axis. The plotted points represent samples whose viral loads exceeded the detection limits (Table 5), their color defines which herpesvirus that point belongs to: EBV (blue), CMV (red), HHV6 (green), HHV7 (yellow) and KSV (gray). However, only those points with a circle represent samples whose viral loads exceeded some clinical threshold. This graph shows a sample belonging to patient TR13 whose viral loads exceeded the established clinical threshold for more than one Herpesvirus, specifically for EBV, HHV6 and HHV7 viruses.

Of 349 samples analyzed, one sample belonging to patient TR13 showed viral loads that exceeded the thresholds established for EBV, HHV6 and HHV7 viruses, being the only sample in which co-infection events were found (FIG. 8).

Calculation of the Specificity of the Test

To more fully assess the specificity of the proposed technique, the probability that the viral load found in a given sample was actually derived from the identified virus and not from any other involved in the present method was calculated. For this, those viruses with viral load (EBV, CMV, HHV6 and HHV7) and those samples in which co-infection events of at least 2 viruses exceeding the established clinical thresholds were considered. The specificity value was calculated as an average of proportions from the following formula:

Average[Viral load of virus $A$(monoinfection)/Viral load of virus $A$ plus any other positive load(s) found(di-infection or tri-infection)]

High specificity was found for all viruses (Table 16).

TABLE 16

Specificity of the test for each virus

| Virus | Specificity (proportion) |
|---|---|
| VEB | 0.82 |
| CMV | 1 |
| HHV6 | 0.89 |
| HHV7 | 0.89 |

CONCLUSIONS

Of the samples analyzed, 34 (10%) showed at least one point whose viral load exceeded any of the established clinical thresholds; 16 of them presented sustained high viral loads in contiguous times. The highest viral loads observed were 82,470 copies/µg for HHV7, 7,170 copies/µg for HHV6 and 2,740 copies/µg for CMV. HHV7 was the agent that most frequently exceeded the established threshold (18 points), followed by CMV (10 points) and HHV6 (7 points). In conclusion, the method developed in this work was useful in detecting the 5 herpesviruses under study in a group of post-transplant pharmacologically immunosuppressed patients. The timely detection of viral loads is of great importance since it guides antiviral treatment and in the case of transplant patients it is essential for the administration of adequate doses of immunosuppressive drugs.

REFERENCES

1. Informe anual 2015. GODT Global Observatory on Donation and Transplantation [Internet]. 2017. Available from: transplant-observatory.org/2015-activity-data/.
2. Yuste J R, del Pozo J L, Quetglas E G, Azanza J R. [The most common infections in the transplanted patient]. Anales del sistema sanitario de Navarra. 2006; 29 Suppl 2:175-205.
3. Bernard Roizman and Philip E. Pellett. The Family Herpesviridae: A Brief Introduction. En Fields virology. 4th ed. Philadelphia: Lippincott-Raven Publishers 2001. p. 2397-446.
4. Boutolleau D, Fernandez C, Andre E, Imbert-Marcille B M, Milpied N, Agut H, et al. Human herpesvirus (HHV)-6 and HHV-7: two closely related viruses with different infection profiles in stem cell transplantation recipients. J Infect Dis. 2003; 187(2):179-86.
5. Gotoh K, Ito Y, Ohta R, Iwata S, Nishiyama Y, Nakamura T, et al. Immunologic and virologic analyses in pediatric liver transplant recipients with chronic high Epstein-Barr virus loads. J Infect Dis. 2010; 202(3):461-9.
6. Kimura H, Morita M, Yabuta Y, Kuzushima K, Kato K, Kojima S, et al. Quantitative analysis of Epstein-Barr virus load by using a real-time PCR assay. J Clin Microbiol. 1999; 37(1):132-6.
7. Mendez J C, Dockrell D H, Espy M J, Smith T F, Wilson J A, Harmsen W S, et al. Human beta-herpesvirus interactions in solid organ transplant recipients. J Infect Dis. 2001; 183(2):179-84.
8. Ono Y, Ito Y, Kaneko K, Shibata-Watanabe Y, Tainaka T, Sumida W, et al. Simultaneous monitoring by real-time polymerase chain reaction of epstein-barr virus, human cytomegalovirus, and human herpesvirus-6 in juvenile and adult liver transplant recipients. Transplant Proc. 2008; 40(10):3578-82.
9. Razonable R R, Brown R A, Humar A, Covington E, Alecock E, Paya C V, et al. Herpesvirus infections in solid organ transplant patients at high risk of primary cytomegalovirus disease. J Infect Dis. 2005; 192(8):1331-9.
10. Chakrabarty A, Pang K R, Wu J J, Narvaez J, Rauser M, Huang D B, et al. Emerging therapies for herpes viral infections (types 1-8). Expert opinion on emerging drugs. 2004; 9(2):237-56.
11. Smith C, Khanna R. Immune regulation of human herpesviruses and its implications for human transplantation. Am J Transplant. 2013; 13 Suppl 3:9-23; quiz
12. Kim H S, Kim D M, Neupane G P, Lee Y M, Yang N W, Jang S J, et al. Comparison of conventional, nested, and real-time PCR assays for rapid and accurate detection of *Vibrio vulnificus*. J Clin Microbiol. 2008; 46(9):2992-8.
13. Pozo F, Tenorio A. Detection and typing of lymphotropic herpesviruses by multiplex polymerase chain reaction. Journal of virological methods. 1999; 79(1):9-19.
14. Soriano-Lopez D P, Alcantar-Fierros J M, Hernandez-Plata J A, Gonzalez-Jorge A L, Velazquez-Ramos S, Flores-Hernandez M A, et al. A Scheduled Program of Molecular Screening for Epstein-Barr Virus Decreases the Incidence of Post-transplantation Lymphoproliferative Disease in Pediatric Liver Transplantation. Transplant Proc. 2016; 48(2):654-7.
15. Wada K, Kubota N, Ito Y, Yagasaki H, Kato K, Yoshikawa T, et al. Simultaneous quantification of Epstein-Barr virus, cytomegalovirus, and human herpesvirus 6 DNA in samples from transplant recipients by multiplex real-time PCR assay. J Clin Microbiol. 2007; 45(5):1426-32.
16. Chan P K, Chik K W, To K F, Li C K, Shing M M, Ng K C, et al. Case report: human herpesvirus 7 associated fatal encephalitis in a peripheral blood stem cell transplant recipient. J Med Virol. 2002; 66(4):493-6.
17. Razonable R R. Human herpesviruses 6, 7 and 8 in solid organ transplant recipients. Am J Transplant. 2013; 13 Suppl 3:67-77; quiz—8.
18. Auten M, Kim A S, Bradley K T, Rosado F G. Human herpesvirus 8-related diseases: Histopathologic diagnosis and disease mechanisms. Seminars in diagnostic pathology. 2017; 34(4):371-6.

19. Viejo-Borbolla A, Ottinger M, Schulz T F. Human herpesvirus 8: biology and role in the pathogenesis of Kaposi's sarcoma and other AIDS-related malignancies. Current HIV/AIDS reports. 2004; 1(1):5-11.
20. Tanaka N, Kimura H, Iida K, Saito Y, Tsuge I, Yoshimi A, et al. Quantitative analysis of cytomegalovirus load using a real-time PCR assay. J Med Virol. 2000; 60(4): 455-62.
21. Hara S, Kimura H, Hoshino Y, Tanaka N, Nishikawa K, Ihira M, et al. Detection of herpesvirus DNA in the serum of immunocompetent children. Microbiol Immunol. 2002; 46(3):177-80.
22. Altschul S F, Gish W, Miller W, Myers E W, Lipman D J. Basic local alignment search tool. J Mol Biol. 1990; 215(3):403-10.
23. Boqué R. El límite de detección de un método analítico. Técnicas de Laboratorio, 2004. 26(296): 878-881.
24. Varela-Fascinetto G, Hernandez-Plata J A, Nieto-Zermeno J, Alcantar-Fierros J M, Fuentes-Garcia V, Castaneda-Martinez P, et al. [Pediatric liver transplant program at Hospital Infantil de Mexico Federico Gomez]. Rev Invest Clin. 2011; 63 Suppl 1:57-61.

The invention claimed is:

1. A method to simultaneously detect, amplify, and quantify, with high specificity, reliability, efficiency, precision, repeatability, reproducibility and analytical sensitivity, the presence of nucleic acids from human herpesviruses of the beta and gamma genera: Epstein-Barr virus (EBV), Cytomegalovirus (CMV), Human herpesvirus type 6 (HHV6), Human herpesvirus type 7 (HHV7) and Kaposi's Sarcoma Virus (KSV) by the real-time multiplex quantitative polymerase chain reaction (PCR) technique comprising:

a) carrying out the amplification reaction in two separate tubes simultaneously in a single run using a hydrolysis probe and primers specific for each target nucleic acid, wherein first reaction comprises amplifying viral genomic fragments of EBV and CMV herpesviruses and a fragment of the endogenous human beta-actin gene; wherein second reaction comprises amplifying three viral genomic fragments of herpesvirus HHV6, HHV7 and KSV, wherein the primers and probe specific for KSV comprise nucleotide sequences selected from the group consisting of SEQ ID NO 16: AGT-TATGGGCGACTGGTCTG, and SEQ ID NO 17: GGATGGAAGACGAGATCCAA, and SEQ ID NO 18: CY5™ (6-6-(2E)-3,3-dimethyl-2-[(2E,4E)-5-(1,3,3-trimethylindol-1-ium-2-yl)penta-2,4-dienylidene]indol-1-yl-5-carboxypentyl)-AAGTCCGTATGGGT-CATTGC-BHQ3a® (3-Diethylamino-5-phenylphenazium-7-diazobenzene-4"-(N-methyl-N-propylamino); and b) quantifying viral load from standard curves constructed with 10-fold to 1,000,000-fold serial dilutions of plasmids containing viral genomic fragments and 100 ng of DNA from a human cell line negative for all viruses under study, wherein the human cell line is a T cell line;

wherein the amplification conditions are:

i) pre-hold step with Uracil-DNA Glycosylase (UDG) is carried out at a temperature of 52° C. for 2.5 minutes with a single cycle being performed;

ii) hold step for viral DNA denaturation is carried out at a temperature of 95° C. for 15 minutes, performing a single cycle;

iii) cycling step for viral DNA denaturation, primers annealing and PCR product extension is carried out at 95° C. for 15 seconds and 60° C. for one minute, performing 50 cycles;

wherein a detection range for a number of viral particles of the human herpesviruses of the beta and gamma genera in a co-infected sample is between 21 and one million, wherein the lowest detection range for EBV is 21;

wherein the lowest detection range for HHV6 is 21;
wherein the lowest detection range for CMV is 24;
wherein the lowest detection range for HHV7 is 33; and
wherein the lowest detection range for KSV is 29.

2. The method according to claim 1, wherein the first reaction, in addition to detecting viruses, further comprises assessing, through the amplification of the beta-actin human endogenous gene, the presence of inhibitors of the DNA protein polymerase and DNA integrity of the biological sample and thus works as an internal control of the PCR and as a control of the amplifiability of the sample.

3. The method according to claim 1, wherein probes labeled with the fluorophores FAM™ (3',6'-Dihydroxy-3-oxo-3H-spiro[2-benzofuran-1,9'-xanthene]-6-carboxyl) fluorescent dye, JOE™ (4',5'-Dichloro-3',6'-dihydroxy-2',7'-dimethoxy-3-oxo-3H-spiro[2-benzofuran-1,9'-xanthene]-6-carboxyl) fluorescent dye and CY5™ (6-6-(2E)-3,3-dimethyl-2-[(2E,4E)-5-(1,3,3-trimethylindol-1-ium-2-yl)penta-2,4-dienylidene]indol-1-yl-5-carboxypentyl) fluorescent dye are used for the EBV, CMV and beta-actin targets respectively from the first reaction, or for the HHV6, HHV7 and KSV respectively of the second reaction.

* * * * *